(12) United States Patent
Zaitsu

(10) Patent No.: US 11,305,117 B2
(45) Date of Patent: Apr. 19, 2022

(54) TERMINAL DEVICE, CONTROL METHOD, PROGRAM, AND TREATMENT SYSTEM

(71) Applicant: OMRON HEALTHCARE Co., Ltd., Kyoto (JP)

(72) Inventor: Kenichiro Zaitsu, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 20 days.

(21) Appl. No.: 16/734,575

(22) Filed: Jan. 6, 2020

(65) Prior Publication Data

US 2020/0139117 A1 May 7, 2020

Related U.S. Application Data

(63) Continuation of application No. PCT/JP2018/022369, filed on Jun. 12, 2018.

(30) Foreign Application Priority Data

Jul. 27, 2017 (JP) .............................. JP2017-145456

(51) Int. Cl.
*A61N 1/36* (2006.01)
*A61N 1/04* (2006.01)
*A61N 1/32* (2006.01)

(52) U.S. Cl.
CPC ......... *A61N 1/3603* (2017.08); *A61N 1/0456* (2013.01); *A61N 1/322* (2013.01)

(58) Field of Classification Search
CPC .... A61N 1/3603; A61N 1/0456; A61N 1/322; A61N 1/08; A61N 1/32
See application file for complete search history.

(56) References Cited

U.S. PATENT DOCUMENTS

2013/0085538 A1 4/2013 Volpe et al.
2014/0206974 A1 7/2014 Volpe et al.
(Continued)

FOREIGN PATENT DOCUMENTS

JP H0454974 A 2/1992
JP 3153006 U 8/2009
(Continued)

OTHER PUBLICATIONS

International Search Report of the International Searching Authority for PCT/JP2018/022369 dated Sep. 4, 2018.
(Continued)

*Primary Examiner* — Alyssa M Alter
(74) *Attorney, Agent, or Firm* — Birch, Stewart, Kolasch & Birch, LLP

(57) ABSTRACT

A terminal device, a control method, a treatment system, and a non-transitory computer-readable medium, with the terminal device being configured to wirelessly communicate with an electrical treatment device. A terminal device is configured to wirelessly communicate with electrical treatment devices. Each one of the electrical treatment devices comprises a case and a vibration source that vibrates the case. The terminal device comprises a display control unit that displays image information associated with the each one of the electrical treatment devices on a display of the terminal device; a vibration instruction unit that instructs one of the electrical treatment devices associated with image information selected by a user to vibrate the case; and a treatment content setting unit that sets a treatment content performed by the each one of the electrical treatment devices in accordance with an instruction from the user notified by vibration of the case.

9 Claims, 10 Drawing Sheets

(56) References Cited

U.S. PATENT DOCUMENTS

| | | |
|---|---|---|
| 2015/0164427 A1 | 6/2015 | Volpe et al. |
| 2017/0128722 A1 | 5/2017 | Perez |
| 2018/0000347 A1* | 1/2018 | Perez .................. A61B 5/0024 |
| 2018/0132792 A1 | 5/2018 | Volpe et al. |

FOREIGN PATENT DOCUMENTS

| | | | |
|---|---|---|---|
| JP | 2014526282 A | 10/2014 | |
| WO | WO-2010051388 A1 * | 5/2010 | ......... A61N 1/36146 |

OTHER PUBLICATIONS

Translation of the International Search Report of the International Searching Authority for PCT/JP2018/022369 dated Sep. 4, 2018.
German Office Action for German Application No. 112018003098.9, dated Dec. 3, 2021, with an English translation.

* cited by examiner

TERMINAL DEVICE, CONTROL METHOD, PROGRAM, AND TREATMENT SYSTEM

CROSS-REFERENCE TO RELATED APPLICATIONS

This is a continuation of International Application PCT/JP2018/022369, with an international filing date of Jun. 12, 2018, filed by applicant, the disclosure of which is hereby incorporated by reference in its entirety.

TECHNICAL FIELD

The present disclosure relates to a terminal device, a control method, a program, and a treatment system, with the terminal device being configured to wirelessly communicate with an electrical treatment device.

BACKGROUND ART

A known electrical treatment device provides electrical stimulation to muscles within the body via electrodes attached to the surface regions of the body, such as the abdomen and the back. A known method of notifying a user of such an electrical treatment device of various information includes a technology employing a vibration unit such as a vibrator.

For example, JP 2014-526282 T (Patent Document 1) describes a technology of providing a haptic notification to a user via a vibrating alarm module, notifying of an electrical stimulation via a treatment electrode.

CITATION LIST

Patent Literature

Patent Document 1: JP 2014-526282 T

SUMMARY OF INVENTION

Technical Problem

Here, a case is assumed where a plurality of electrical treatment devices (conductive pads) are used to treat multiple sites of the body. In this case, the electrical treatment devices and a control device that provides instructions to the electrical treatment devices have a wireless connection, meaning that the wires cannot be followed as with a configuration with a wired connection. Thus, which treatment site the electrical treatment device the user wants to control is attached to cannot be easily determined. Accordingly, in a configuration in which the electrical treatment devices and the control device are wirelessly connected, a setting mistake may occur such as the user setting treatment content intended for the arm as treatment content of the electrical treatment device attached to the waist.

An object of an embodiment of the present disclosure is to provide a terminal device, a control method, a program, and a treatment system that can prevent a setting mistake of the treatment content of electrical treatment devices, with the terminal device being configured to wirelessly communicate with the electrical treatment devices.

Solution to Problem

According to an embodiment, a terminal device is provided that is configured to wirelessly communicate with electrical treatment devices. Each one of the electrical treatment devices comprises a case and a vibration source configured to vibrate the case. The terminal device comprises a display control unit configured to display image information associated with the each one of the electrical treatment devices on a display of the terminal device, a vibration instruction unit configured to instruct one of the electrical treatment devices associated with image information selected by a user to vibrate the case, and a treatment content setting unit configured to set a treatment content performed by the each one of the electrical treatment devices in accordance with an instruction from the user notified by vibration of the case.

The terminal device preferably further comprises a treatment instruction unit configured to instruct the each one of the electrical treatment devices to treat the user in accordance with a treatment content corresponding to the each one of the electrical treatment devices.

Preferably, the treatment content setting unit swaps a first treatment content corresponding to a first electrical treatment device of the electrical treatment devices and a second treatment content corresponding to a second electrical treatment device of the electrical treatment devices in accordance with an instruction from the user. When the first treatment content and the second treatment content have been swapped, the treatment instruction unit instructs the first electrical treatment device and the second electrical treatment device to treat the user in accordance with the first treatment content and the second treatment content which have been swapped.

Preferably, when one of the electrical treatment devices is performing treatment in accordance with the treatment content set by the treatment content setting unit, the vibration instruction unit instructs the one of the electrical treatment devices to vibrate the case on the basis of image information associated with the one of the electrical treatment device being selected.

The treatment content comprises a treatment mode in which a weak electrical stimulation is provided to a treatment site.

Preferably, when image information associated with a predetermined electrical treatment device of the electrical treatment devices is associated with a predetermined treatment content, the treatment content setting unit sets the predetermined treatment content as a treatment content performed by the predetermined electrical treatment device.

According to another embodiment, a control method of a terminal device is provided, the terminal device being configured to wirelessly communicate with electrical treatment devices. Each one of the electrical treatment devices comprises a case and a vibration source configured to vibrate the case. The control method comprises displaying image information associated with the each one of the electrical treatment devices, instructing one of the electrical treatment devices associated with image information selected by a user to vibrate the case, and setting a treatment content performed by the each one of the electrical treatment devices in accordance with an instruction from the user notified by vibration of the case.

According to yet another embodiment, a non-transitory recording medium storing a program is provided that is executed by a computer of a terminal device configured to wirelessly communicate with electrical treatment devices. Each one of the electrical treatment devices comprises a case and a vibration source configured to vibrate the case. The non-transitory recording medium storing a program causes a computer to execute displaying image information associated with the each one of the electrical treatment devices, instructing one of the electrical treatment devices associated with image information selected by a user to vibrate the case, and setting a treatment content performed by the each one of the electrical treatment devices in accordance with an instruction from the user notified by vibration of the case.

According to yet another embodiment, a treatment system comprises electrical treatment devices, and a terminal device configured to wirelessly communicate with the electrical treatment devices. Each one of the electrical treatment devices comprises a case and a vibration source configured to vibrate the case. The terminal device comprises a display control unit configured to display image information associated with the each one of the electrical treatment devices on a display of the terminal device, a vibration instruction unit configured to instruct one of the electrical treatment devices associated with image information selected by a user to vibrate the case, and a treatment content setting unit configured to set a treatment content performed by the each one of the electrical treatment devices in accordance with an instruction from the user notified by vibration of the case.

Advantageous Effects of Invention

According to the present disclosure, with a configuration in which electrical treatment devices are wirelessly connected, a setting mistake of the treatment content of the electrical treatment devices can be prevented.

DESCRIPTION OF EMBODIMENTS

Embodiments of the present invention will be described below with reference to the drawings. In the following description, like components are given like numerals. Names and functions thereof are also the same. Thus, the detailed description of such components is not repeated.

System Configuration

Figure 1:
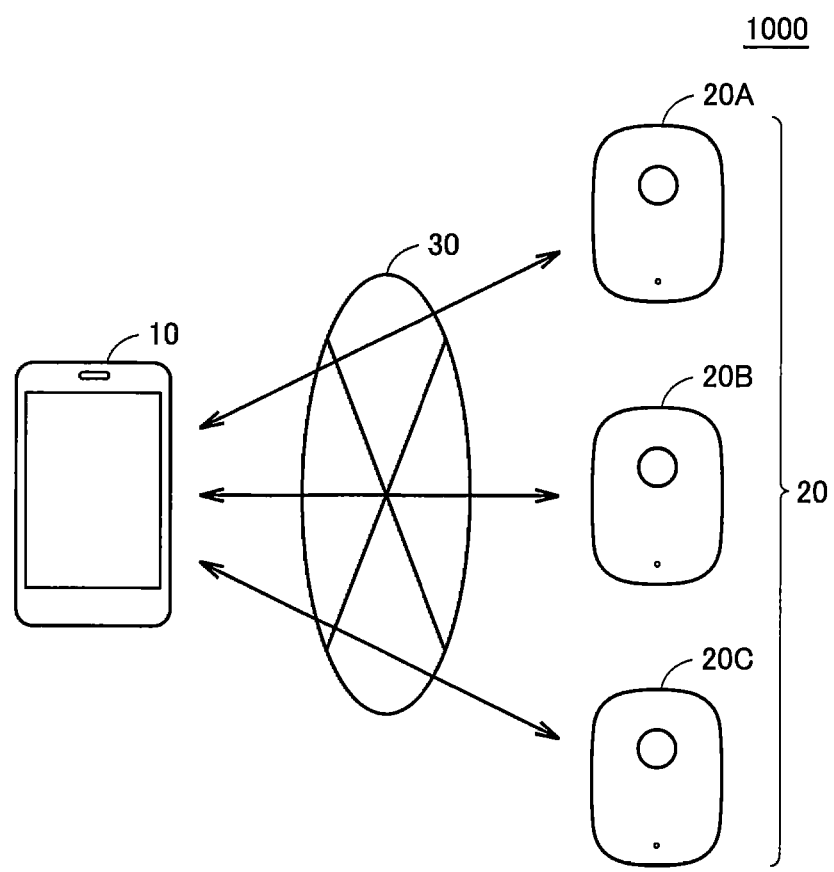
FIG. 1 is a diagram illustrating a schematic configuration of a treatment system.

FIG. 1 is a diagram illustrating a schematic configuration of a treatment system 1000. Referring to FIG. 1, the treatment system 1000 includes a terminal device 10, which is a user terminal, electrical treatment devices 20A, 20B, 20C and a network 30. Hereinafter, when describing configurations and functions shared by the electrical treatment devices 20A, 20B, 20C, the electrical treatment devices 20A, 20B, 20C are collectively referred to as an "electrical treatment device 20".

The electrical treatment device 20 is a cordless type and includes a pad, a holder, and a main body portion that serve as a single unit when used. These portions are used in combination to provide treatment. The electrical treatment device 20 according to the present embodiment is a low-frequency treatment device that provides treatment such as easing user shoulder stiffness by supplying a low-frequency pulse. For example, the frequency of the low-frequency pulse current is from 1 Hz to 1200 Hz. However, the electrical treatment device 20 may be configured to use a pulse current of other frequency bands. In FIG. 1, only the main body portion of the electrical treatment device 20 is illustrated, and the pad and the holder are omitted from the diagram. The specific configuration of the electrical treatment device 20 will be described later.

The terminal device 10 is, for example, a smart phone including a touch panel. In the description hereinafter, a smart phone will be used as a representative example of the "terminal device". However, the terminal device may be a different terminal device such as a folding type mobile telephone, a tablet terminal device, a personal computer (PC), and a personal data assistance (PDA).

The network 30 for connecting the terminal device 10 and the electrical treatment device 20 employs a short-range wireless communication system, typically BLUETOOTH low energy (BLE). As such, the terminal device 10 and the electrical treatment device 20 are BLE devices having a function of performing wireless communication using BLE. However, the network 30 is not limited thereto, and a different wireless communication system, such as BLUETOOTH or a wireless local area network (LAN), may be employed.

In the treatment system 1000 according to the present embodiment, the terminal device 10 gives instructions to the electrical treatment devices 20A, 20B, 20C paired therewith via an application installed on the terminal device 10. The terminal device 10 displays various kinds of information on the display of the terminal device 10 and notifies the user of necessary information. Specific operations will be described in detail below.

Configuration of Electrical Treatment Device 20

Figure 2:
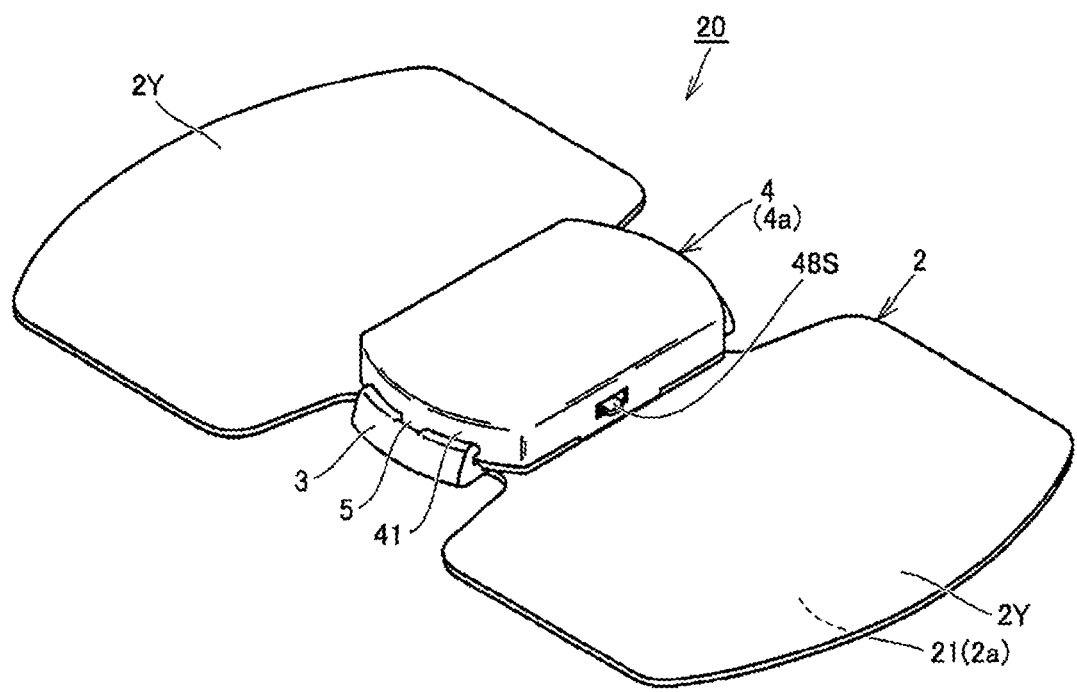
FIG. 2 is a perspective view illustrating an example of a configuration of an electrical treatment device.
Figure 3:
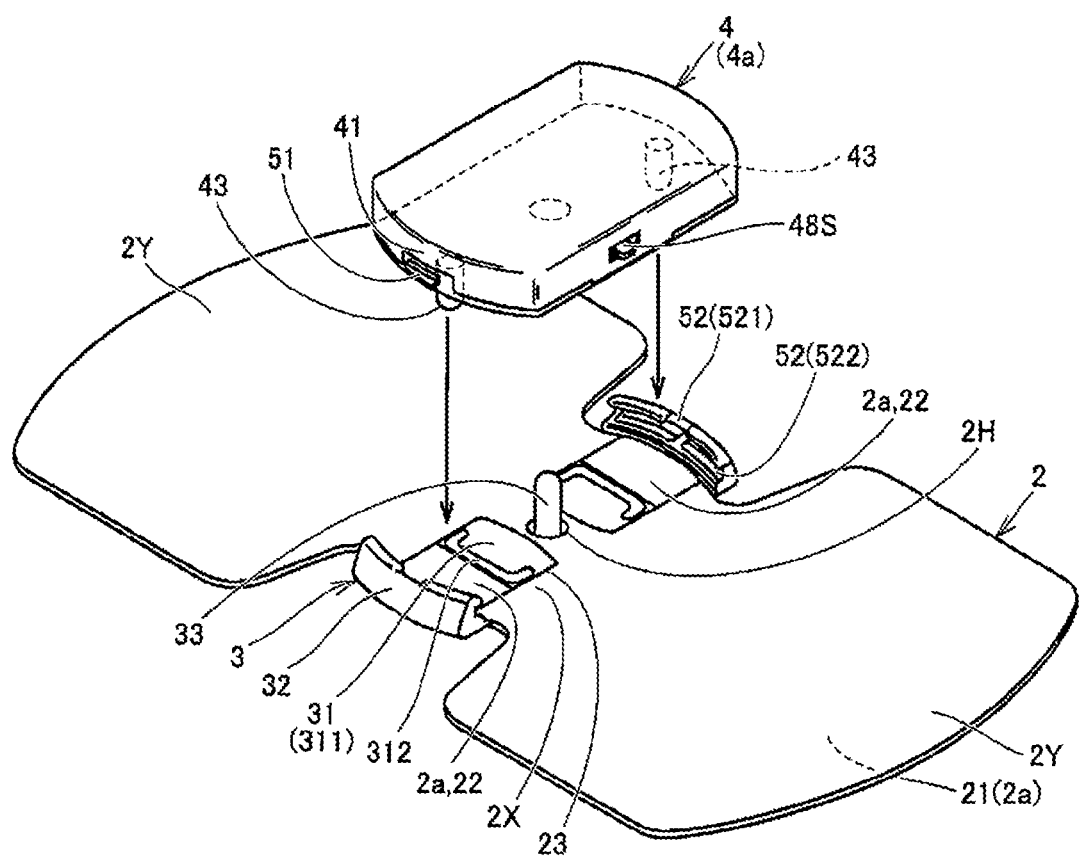
FIG. 3 is a perspective view illustrating a main body portion, a holder, and a pad of the electrical treatment device in a state where the main body portion is separated from the holder and the pad.

FIG. 2 is a perspective view illustrating an example of a configuration of the electrical treatment device 20. FIG. 3 is a perspective view illustrating a main body portion 4, a holder 3, and a pad 2 of the electrical treatment device 20 in a state where the main body portion 4 is separated from the holder 3 and the pad 2.

Referring to FIGS. 2 and 3, the electrical treatment device 20 is a so-called cordless type low-frequency treatment device and includes the pad 2, the holder 3, and the main body portion 4.

The pad 2 has a sheet-like shape and is configured to attach to the user's body. A conductive layer 2a is provided on a body-side portion 21 surface (lower surface), of the outer surfaces of the pad 2, that faces the body. The pad 2 is attached to the user's skin by using a conductive gel or the like, and a low-frequency pulse is supplied to the user through the conductive layer 2a.

Referring to FIG. 3, the pad 2 includes an attachment portion 2X and a treatment portion 2Y. The attachment portion 2X is held by the holder 3. A window portion 23 and a through hole 2H are provided at the attachment portion 2X. A positioning protrusion 312 of the holder 3 is disposed on the inside of the window portion 23. An interlock pin 33 of the holder 3 is inserted through the through hole 2H. The treatment portion 2Y is provided on both the left and right sides of the attachment portion 2X, and the conductive layer 2a is exposed on the body-side portion 21 of the treatment portion 2Y.

The conductive layer 2a is also exposed on the surface facing the main body portion 4 at the attachment portion 2X, and the exposed portion constitutes a pad side electrode portion 22. The pad side electrode portion 22 is formed to establish an electrical connection with a main body portion side electrode portion 43, and a conductive layer 2a corresponding to one electrode portion (for example, a positive electrode) is exposed at one end of the attachment portion 2X, and a conductive layer 2a corresponding to another electrode portion (for example, a negative electrode) is exposed at the other end of the attachment portion 2X.

Referring to FIG. 3, the holder 3 includes a pad holding portion 31 with a plate-like shape and a pair of wall portions 32 erected from both ends of the pad holding portion 31. An attachment portion 2X of the pad 2 is disposed on an upper surface 311 of the pad holding portion 31. Double-sided adhesive tape, glue, adhesive, or the like is disposed, as necessary, between the upper surface 311 and the attachment portion 2X.

The positioning protrusion 312 is provided on the pad holding portion 31. By fitting the inner peripheral edge of the window portion 23 provided in the pad 2 to the positioning protrusion 312, the pad 2 can be positioned with respect to the holder 3. The interlock pin 33 is centrally disposed on the pad holding portion 31. When attaching the pad 2 to the holder 3, the interlock pin 33 is inserted into the through hole 2H.

The pad 2 is a consumable item, and the pad 2 can be detachably attached to the main body portion 4, thus allowing replacement of the pad 2. In the present embodiment, the holder 3 holds the pad 2 such that the holder 3 and the pad 2 are integrated, and the main body portion 4 is configured to be detachably attached to the pad 2 and the holder 3. The pad 2 can be replaced together with the holder 3, or it is also possible to reuse the holder 3 as necessary.

Referring to FIGS. 2 and 3, the main body portion 4 includes as an outer cover a case 4a with a substantially rectangular parallelepiped shape. A guiding/engagement portion 5 (FIG. 2) is formed between the case 4a and the holder 3, and the main body portion 4 (case 4a) is detachably attached to the holder 3. The guiding/engagement portion 5 includes a protrusion 51 (FIG. 3) formed on a side surface 41 of the case 4a and a groove portion 52 (FIG. 3) formed in each of the wall portions 32 of the holder 3.

Referring to FIG. 3, the groove portion 52 includes a vertical groove portion 521 and a lateral groove portion 522. The vertical groove portion 521 is formed in the vertical direction and opens upward. The lateral groove portion 522 is formed in the lateral direction and opens at both ends. When the main body portion 4 is attached to the holder 3, both of the protrusion 51 and the groove portion 52 move closer together in a facing direction and engage together. By rotating and moving the main body portion 4 with respect to the holder 3, the engagement between the two is released, and the main body portion 4 can be removed from the holder 3.

With the main body portion 4 attached to the holder 3, the main body portion 4 supplies a low-frequency pulse current to the conductive layer 2a of the pad 2. Specifically, the main body portion 4 includes a pair of the main body portion side electrode portions 43, a substrate (not illustrated), an electric circuit (not illustrated), and an interlock mechanism (not illustrated). The electric circuit includes various control devices and is mounted on the surface of the substrate.

Examples of the control devices include a processor for performing various processes, a memory for storing programs, data, and the like, a communication interface for wirelessly communicating various types of data with the terminal device 10, a waveform generation output circuit for boosting the power source voltage and generating and outputting a low-frequency pulse current (treatment current), and a vibrator functioning as a vibration source. The vibrator includes a vibration motor and a drive circuit for the vibration motor. The vibrator vibrates the case 4a by driving the vibration motor. The vibrator is configured to apply a constant vibration to the case 4a, but the amount of vibration can be adjusted as appropriate by changing the amount of power supplied to the vibrator. In addition, the vibration timing (vibration pattern) of the vibrator may be adjusted as appropriate. The vibration source may also not be a vibrator.

The substrate, the electric circuit, and the interlock mechanism are provided inside the main body portion 4 (case 4a). A power source (not illustrated) such as a battery is also provided inside the main body portion 4 (case 4a). A switch 48S (FIG. 2), a display portion (not illustrated) such as light emitting diode (LED), and a button (not illustrated) are provided on the outside of the case 4a.

In a state in which the main body portion 4 is attached to the holder 3, an end portion of the main body portion side electrode portion 43 abuts the pad side electrode portion 22. Thus, the main body portion side electrode portion 43 and the pad side electrode portion 22 are electrically connected, whereby the electric circuit can supply a low-frequency pulse current to the pad side electrode portion 22.

Configuration of Terminal Device 10

Figure 4:
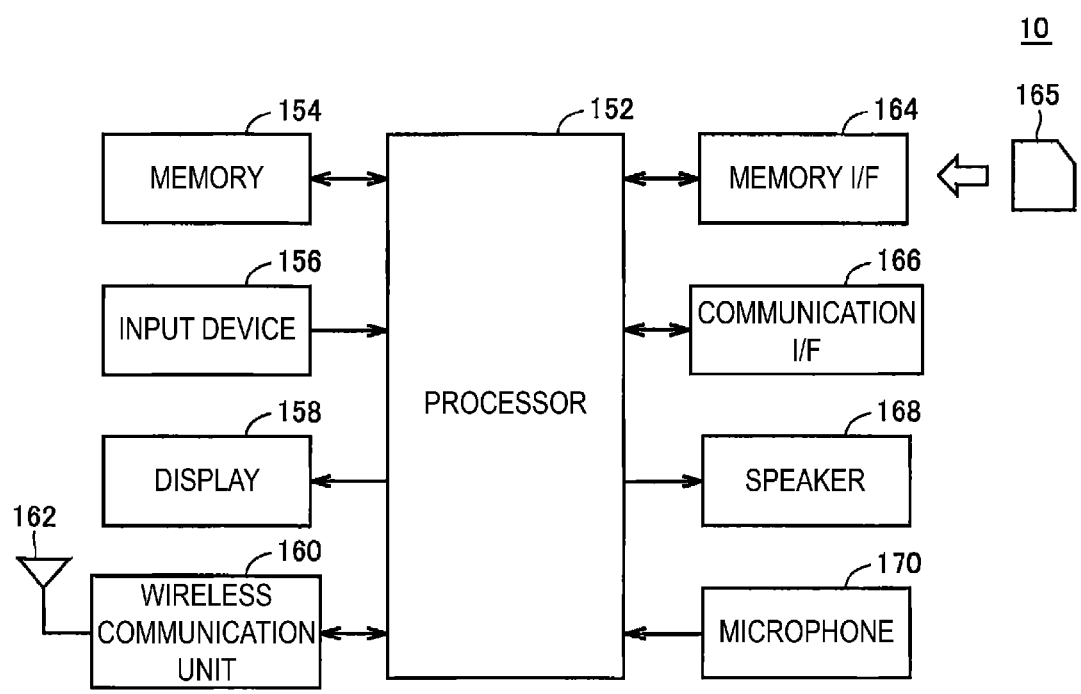
FIG. 4 is a block diagram illustrating an example of a hardware configuration of a terminal device.

FIG. 4 is a block diagram illustrating an example of a hardware configuration of the terminal device 10. Referring to FIG. 4, the terminal device 10 includes, as main components, a processor 152, a memory 154, an input device 156, a display 158, a wireless communication unit 160, a memory interface (I/F) 164, a communication interface (I/F) 166, a speaker 168, and a microphone 170.

The processor 152 typically may be an arithmetic processing unit such as a central processing unit (CPU) or a multi processing unit (MPU). The processor 152 functions as a control unit that controls the operation of components of the terminal device 10 by reading out and executing a program stored in the memory 154. By executing the program, the processor 152 executes processing (steps) of the terminal device 10 described later.

The memory 154 is realized by random access memory (RAM), read-only memory (ROM), flash memory, and the like. The memory 154 stores programs executed by the processor 152, data used by the processor 152, and the like.

The input device 156 receives an operation input to the terminal device 10. Typically, the input device 156 is realized by a touch panel. The touch panel is provided on the display 158 that functions as a display portion, and is, for example, an electrostatic capacitive type. The touch panel detects touch operations on the touch panel by an external object at predetermined intervals of time and inputs touch coordinates to the processor 152. However, the input device 156 may include a button or the like.

The wireless communication unit 160 connects to a mobile communication network via a communication antenna 162 and transmits and receives signals for wireless communication. Accordingly, the terminal device 10 can communicate with other communication devices via a mobile communication network such as Long Term Evolution (LTE), for example.

The memory interface 164 reads data from an external storage medium 165. The processor 152 reads the data stored in the storage medium 165 via the memory interface 164 and stores the data in the memory 154. The processor 152 reads the data from the memory 154 and stores the data in the external storage medium 165 via the memory interface 164.

The storage medium 165 may also be a medium that store programs in a non-volatile manner, such as a compact disc (CD), digital versatile disk (DVD), BLU-RAY disc (BD), universal serial bus (USB) memory, and secure digital (SD) memory card.

The communication interface (I/F) 166 is a communication interface for exchanging various data between the terminal device 10 and the electrical treatment device 20 and is realized by an adapter, a connector, or the like. As the communication method, for example, a wireless communication method such as BLUETOOTH low energy (BLE) and wireless LAN may be employed.

The speaker 168 converts an audio signal from the processor 152 to voice and outputs the same to the outside of the terminal device 10. The microphone 170 receives an audio input for the terminal device 10 and provides to the processor 152 an audio signal corresponding to the audio input.

System Operation Summary

An operation overview of the treatment system 1000 will be described with reference to FIGS. 5 to 8. Note that the screens illustrated in FIGS. 5 to 8 are screens displayed on the display 158 after activating an application for electrical treatment installed on the terminal device 10 (hereinafter, also simply referred to as a "treatment app"). Various types of image information are displayed on the display 158. Image information includes symbols, characters, graphics, and combinations thereof.

Setting of Treatment Content

Figure 5:
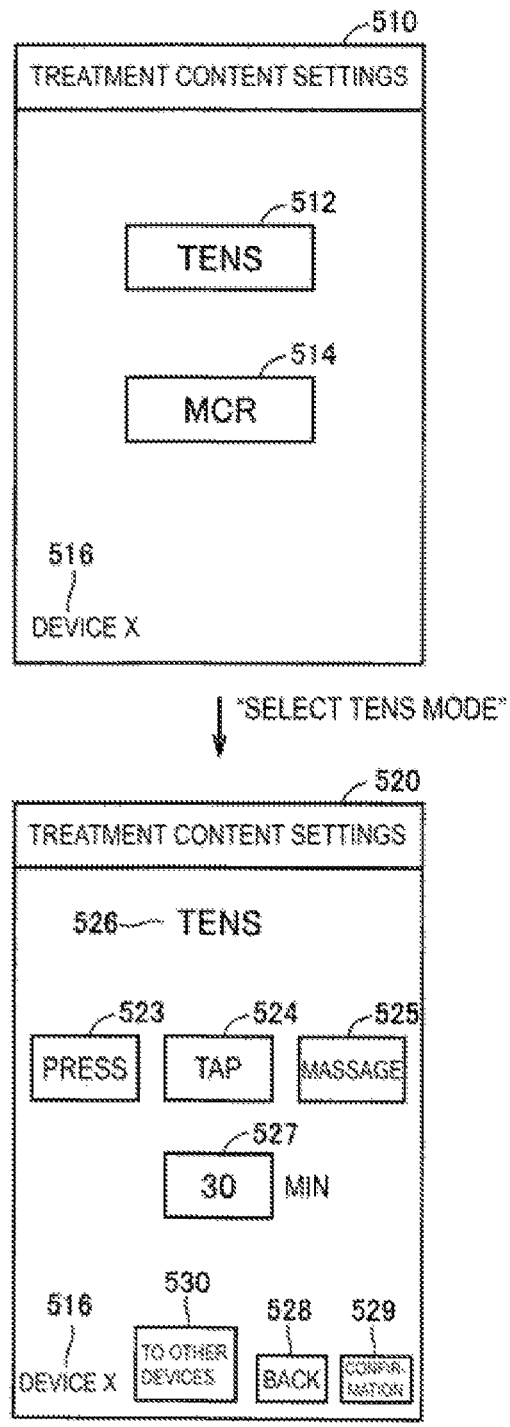
FIG. 5 is a diagram illustrating an example of a settings screen of a treatment content.

FIG. 5 is a diagram illustrating an example of a settings screen of the treatment content. In this example, the terminal device 10 has paired with the electrical treatment device 20 and a wireless communication connection between the terminal device 10 and the electrical treatment device 20 has been established. Also, the user has the pad 2 of each of the three electrical treatment devices 20A, 20B, 20C attached to the respective desired treatment site.

Referring to FIG. 5, a mode selection button 512 for selecting a transcutaneous electrical nerve stimulation (TENS) mode and a mode selection button 514 for selecting a microcurrent (MCR) mode are displayed on a settings screen 510. In addition, a character string 516 in FIG. 5 is a character string image indicating that the treatment content settings screen is for a device X. For example, the electrical treatment devices 20A, 20B, 20C are associated with devices X, Y, Z (see FIG. 6 described below) on a treatment app screen. Note that the user does not know that the electrical treatment devices 20A, 20B, 20C are associated with devices X, Y, Z on a treatment app screen. Thus, the user cannot determine which pad 2 attached to which treatment site corresponds to the electrical treatment device 20 that is the device X.

Thus, when the terminal device 10 receives a selection operation (tap operation) of the character string 516, the terminal device 10 instructs the electrical treatment device 20A associated with the device X to vibrate the case 4a by running the vibrator. The case 4a of the electrical treatment device 20A vibrating allows the user to determine which pad 2 of the electrical treatment device 20A associated with the device X is attached to which treatment site. When the treatment site is the waist, the user may set the treatment content for the waist as the treatment content for the device X.

The TENS mode is a mode in which electrical stimulation is provided to a sensory nerve to reduce or suppress pain. The MCR mode is a mode in which a microcurrent is run into the body to stimulate muscles and repair cells. Typically, the microcurrent is a current low enough to not cause muscle contraction and may be from 50 μA to 500 μA, for example. In a case where the user selects the TENS mode, when the terminal device 10 receives selection of the mode selection button 512, the terminal device 10 displays a settings screen 520.

The settings screen 520 is a course selection screen for the TENS mode. Specifically, a character string 526 indicating that this is a TENS mode settings screen, and course selection buttons 523, 524, 525 for selecting courses including "press", "tap", and "massage" respectively are displayed on the settings screen 520. Furthermore, a settings button 527 for setting the treatment time is displayed on the settings screen 520. In this example, the user selects the course "tap" and sets the treatment time to "10 min". In the following description, the treatment content with the mode set to "TENS", the course set to "tap", and the treatment time set to "10 min" is also referred to as a treatment content Ta. Note that when a back button 528 is selected, the settings screen 510 is displayed.

The treatment contents for the other devices Y and Z are set in a similar manner. For example, when the user selects a button 530 for setting the treatment content of other devices, a pop-up menu for selecting the target device to be set is displayed, and the user selects the character string "device Y" (or the character string "device Z") from the pop-up menu. In the case where the character string "device Y" is selected, the settings screen (screen similar to the settings screen 510) for the treatment content of the device Y is displayed. For example, in this case, the treatment content of the device Y is set to a treatment content Tb (mode: "TENS", course: "massage", treatment time: "5 min"), and the treatment content of device Z is set to a treatment content Tc (mode: "TENS", course: "press", treatment time: "30 min"). A confirmation screen 610 is displayed when a confirmation button 529 is selected for confirmation of the treatment content.

Confirmation of Treatment Content

Figure 6:
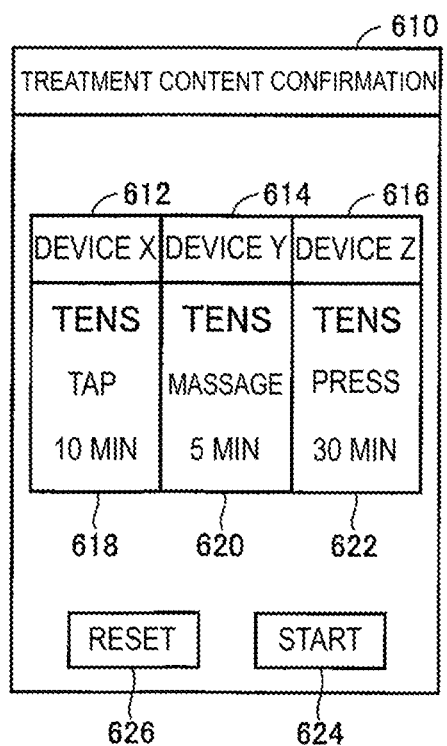
FIG. 6 is a diagram illustrating an example of a confirmation screen of a treatment content.

FIG. 6 is a diagram illustrating an example of a confirmation screen of the treatment content. Referring to FIG. 6, the confirmation screen 610 includes an object 612 including the character string "device X", an object 614 including a character string "device Y", an object 616 including the character string "device Z", an object 618 including the treatment content Ta, an object 620 including the treatment content Tb, an object 622 including the treatment content Tc, a start button 624, and a reset button 626. Note that the term "object" refers to various kinds of image information including image information for receiving user operations, for presenting information to the user, and for exhibiting a function of a combination thereof.

In the confirmation screen 610, the devices X to Z are displayed associated with their respective treatment content Ta to Tc. This allows the user to confirm the treatment content corresponding to the devices X to Z. Also, when the terminal device 10 receives a tap operation on the object 612, the terminal device 10 instructs the electrical treatment device 20A associated with the device X to vibrate the case 4a. In a similar manner, when the terminal device 10 receives a tap operation on the object 614, the terminal device 10 vibrates the case 4a of the electrical treatment device 20B associated with the device Y; and when the terminal device 10 receives a tap operation on the object 616, the terminal device 10 vibrates the case 4a of the electrical treatment device 20C associated with the device Z. This allows the user to reconfirm whether the desired treatment content is set for each treatment site.

When the terminal device 10 receives selection of the reset button 626, the terminal device 10 displays the settings screen 510. When the terminal device 10 receives selection of the start button 624, the terminal device 10 provides a start treatment instruction to the electrical treatment devices 20A to 20C associated with the devices X to Z. In another possible configuration, a start button is provided for each of the devices X to Z, and the start treatment instruction can be provided to each electrical treatment device 20.

In this example, the user may swap the treatment content associated with a device with the treatment content associated with another device.

Figure 7:
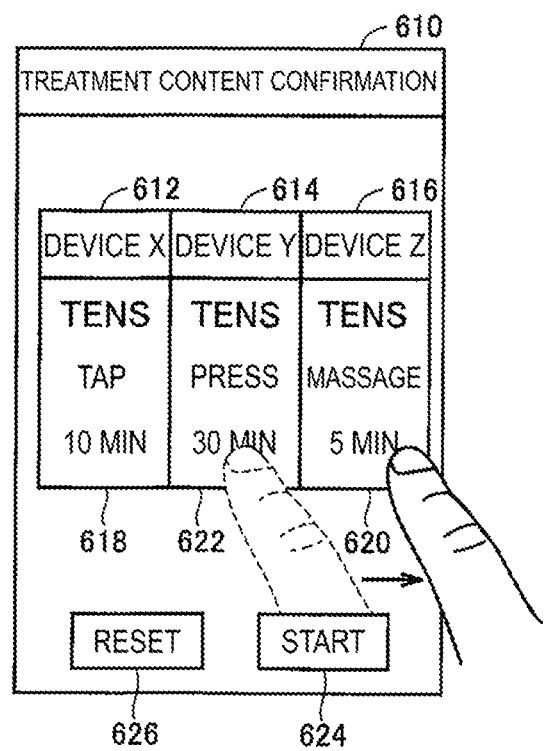
FIG. 7 is a diagram for describing a method of swapping treatment content.

FIG. 7 is a diagram for describing a method of swapping the treatment content. In this example, the user wants to swap the treatment content Tb associated with the device Y and the treatment content Tc associated with the device Z. Referring to FIG. 7, for example, when the user long presses the object 620 including the treatment content Tb and performs a slide operation in the right direction, the object 620 and the object 622 are swapped. That is, the treatment content of the device Y and the treatment content of the device Z are swapped.

Specifically, looking at the confirmation screen 610 in FIG. 6, the treatment content of the device Y prior to swapping is set as the treatment content Tb. However, the treatment content of the device Y after swapping is set as the treatment content Tc (i.e., the treatment content of the device Z prior to swapping). In a similar manner, the treatment content of the device Z after swapping is set as the treatment content of the device Y prior to swapping (i.e., the treatment content Tb). Note that the method of swapping the treatment content is not limited to that described above and a different user interface may be used. For example, a swap button for swapping the treatment contents of the devices may be displayed on the screen, and the treatment content of the devices may be swapped by selecting the swap button.

In this way, the terminal apparatus 10 can swap the treatment content corresponding to the device X (i.e., the electrical treatment device 20A) and the treatment content corresponding to the device Y (i.e., the electrical treatment device 20B) in accordance with a user instruction.

Operation During Treatment

Figure 8:
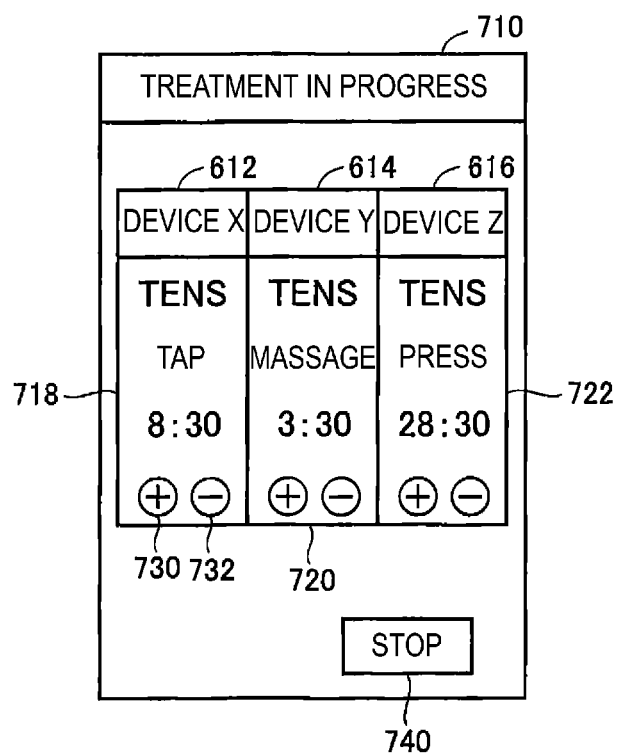
FIG. 8 is a diagram illustrating an example of a screen displayed during treatment.

FIG. 8 is a diagram illustrating an example of a screen displayed during treatment. When selection of the start button 624 on the confirmation screen 610 illustrated in FIG. 6 is received, the terminal device 10 displays an in-treatment screen 710 illustrated in FIG. 8. An object 718 is the same as the object 618 of the confirmation screen 610 (see FIG. 6) except that it additionally includes a button 730 for increasing the stimulation level and a button 732 for decreasing the stimulation level. In a similar manner, an object 720 is the same as the object 620 except that it additionally includes the button 730 and the button 732, and an object 722 is the same as the object 622 except that it additionally includes the button 730 and the button 732. The user can select the buttons 730, 732 to change the stimulation level.

When the terminal device 10 receives selection of a stop button 740, the terminal device 10 provides a stop treatment instruction to all of the electrical treatment devices 20A to 20C associated with the devices X to Z. In another possible configuration, a stop button is provided for each of the devices X to Z, and the stop treatment instruction can be provided to each electrical treatment device 20. The in-treatment screen 710 may also include an end button for providing a treatment end instruction.

During treatment, by receiving a tap operation on the objects 612 to 616, the terminal device 10 can instruct the electrical treatment devices 20A to 20C to vibrate the cases 4a. This is particularly advantageous when the MCR mode is selected. Specifically, in the MCR mode, a microcurrent low enough to not cause muscle contraction is flowing, and the electrical stimulation intensity felt by the user is very low. Thus, in the MCR mode, the user may not feel as though they are being treated. As such, by performing a tap operation on the objects 612 to 616 and causing the cases 4a of the electrical treatment devices 20A to 20C to vibrate, the user can know that treatment in the MCR mode is being performed.

Functional Configuration

Figure 9:
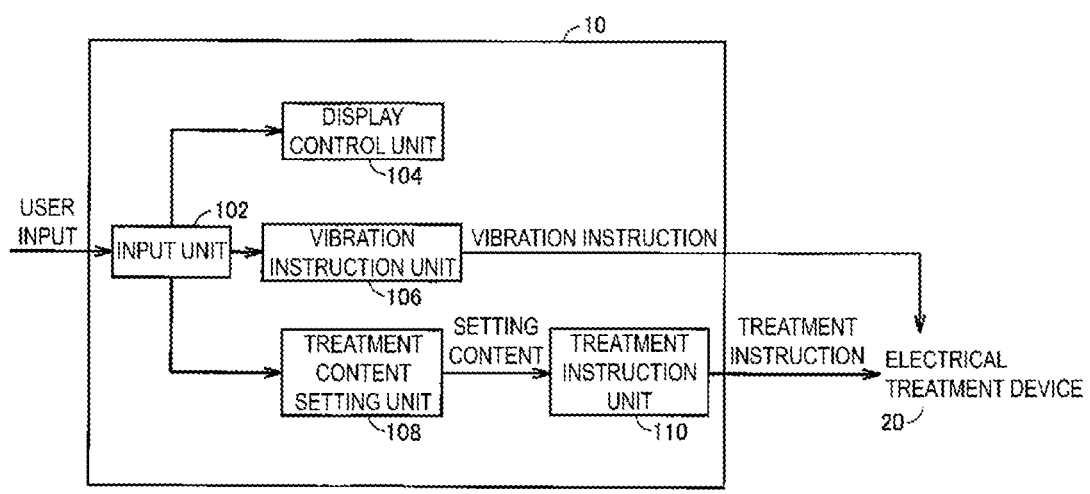
FIG. 9 is a block diagram illustrating an example of a functional configuration of a terminal device.

FIG. 9 is a block diagram illustrating an example of a functional configuration of the terminal device 10. Referring to the diagram, the terminal device 10 includes, as main components, an input unit 102, a display control unit 104, a vibration instruction unit 106, a treatment content setting unit 108, and a treatment instruction unit 110. Each function of the terminal device 10 is realized, for example, by the processor 152 of the terminal device 10 executing a program stored in the memory 154. Note that one or more or all of these functions may be configured to be realized by hardware.

The input unit 102 receives an instruction input from the user via the input device 156. The input unit 102 outputs instruction input information from the user to the display control unit 104, the vibration instruction unit 106, and the treatment content setting unit 108.

The display control unit 104 causes the display 158 to display various types of information. Specifically, the display control unit 104 causes the display 158 to display the settings screen 510, 520, the confirmation screen 610, the in-treatment screen 710, and the like described above. Specifically, the display control unit 104 displays image information associated with each of the electrical treatment devices 20 (for example, the character string 516, and the objects 612, 614 and 616) on the display 158 of the terminal device 10.

The vibration instruction unit 106 instructs the electrical treatment device 20 associated with the image information selected by the user to vibrate the case 4a. Specifically, the vibration instruction unit 106 sends to the electrical treatment device 20 control information for driving the vibrator of the electrical treatment device 20. In some embodiments, when treatment is being performed in accordance with the treatment content corresponding to the electrical treatment device 20, the vibration instruction unit 106 instructs the electrical treatment device 20 to vibrate the case 4a on the basis of the image information associated with the electrical treatment device 20 (for example, the objects 612 to 616) being selected.

The treatment content setting unit 108 sets the treatment content performed by each of the electrical treatment devices 20 in accordance with an instruction from the user who received the notification of the vibrating case 4a. The treatment content includes a treatment mode, a treatment course, and a treatment time. In some embodiments, the treatment content setting unit 108 swaps the treatment content of the electrical treatment devices 20 in accordance with a user instruction. For example, the treatment content setting unit 108 may swap the treatment content corresponding to the electrical treatment device 20B and the treatment content corresponding to the electrical treatment device 20C.

Specifically, in the case where the image information (for example, the object 614) associated with a predetermined electrical treatment device of the electrical treatment devices 20A to 20C (for example, the electrical treatment device 20B) is associated with a predetermined treatment content (for example, the treatment content Tb displayed as the object 620), the treatment content setting unit 108 sets the predetermined treatment content as the treatment content performed by the predetermined electrical treatment device. For example, in the case where the object 622 is associated with the object 612 in accordance with a user instruction, the treatment content Tc ("TENS" for mode, "press" for course, and "30 min" for treatment time) is set to the treatment content of the electrical treatment device 20A.

The treatment instruction unit 110 instructs the electrical treatment devices 20 to treat the user in accordance with the treatment content corresponding to the respective electrical treatment device 20. The treatment instruction unit 110 sends to each electrical treatment device 20 control information causing each treatment content to be performed. In addition, the treatment instruction unit 110 sends various control information to each electrical treatment device 20 in accordance with various instructions from the user (for example, a stimulation level change instruction, and a treatment stop instruction).

Also, when the treatment content of a first electrical treatment device (for example, the electrical treatment device 20A) and the treatment content of a second electrical treatment device (for example, the electrical treatment device 20B) are swapped, the treatment instruction unit 110 instructs the first electrical treatment device and the second electrical treatment device to treat the user in accordance with the treatment contents which have been swapped.

Processing Procedure

Figure 10:
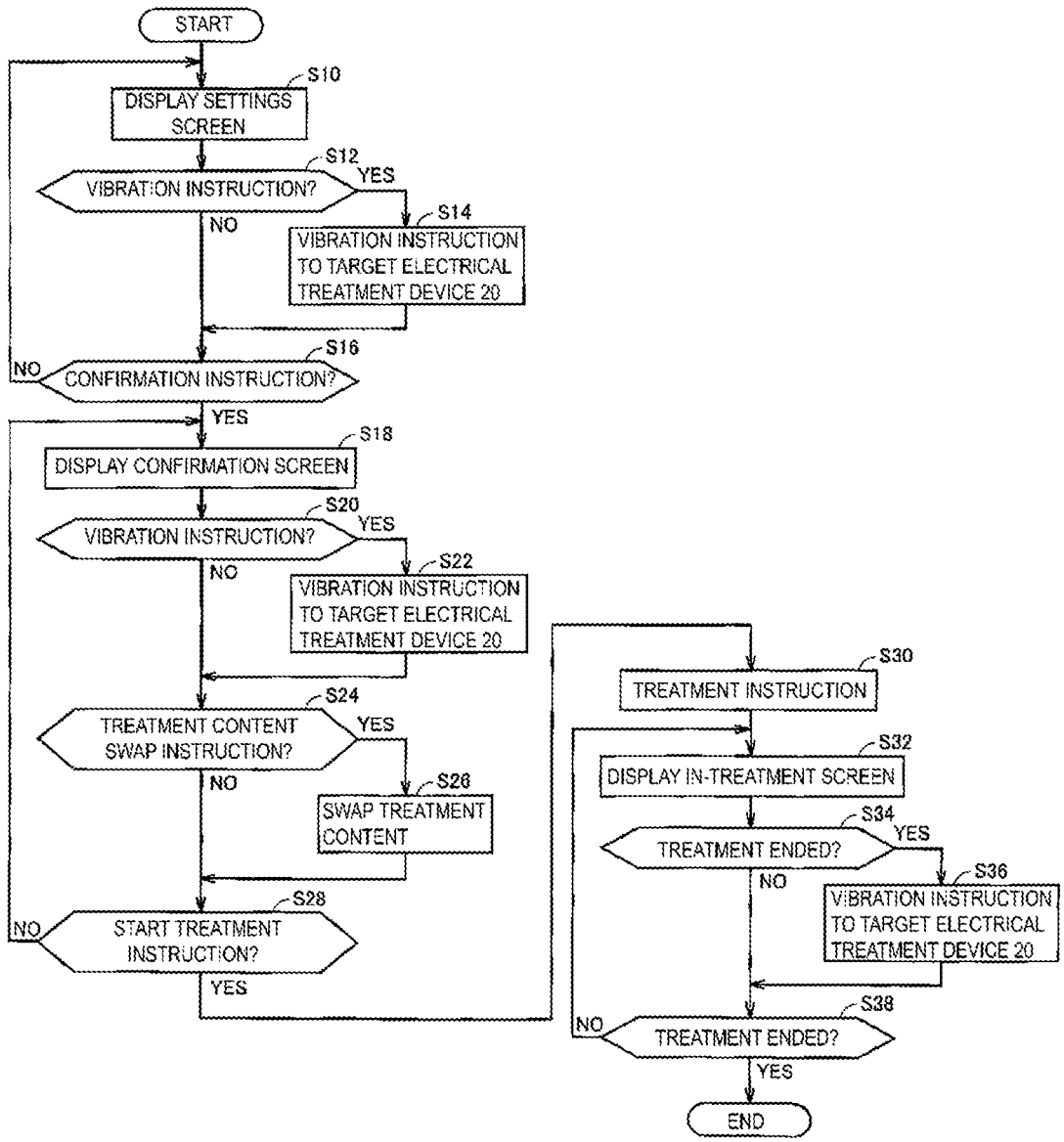
FIG. 10 is a flowchart illustrating an example of a processing procedure of a terminal device.

FIG. 10 is a flowchart illustrating an example of a processing procedure of the terminal device 10. Steps illustrated in FIG. 10 are realized mainly by the processor 152 of the terminal device 10 executing a program (treatment app) stored in the memory 154. At the start time of the flowchart, the terminal device 10 has paired with the electrical treatment device 20 and a wireless communication connection between the terminal device 10 and the electrical treatment device 20 has been established. Also, the user has the pad 2 of each of the three electrical treatment devices 20A, 20B, 20C attached to the respective desired treatment site.

Referring to FIG. 10, the terminal device 10 displays the settings screen (for example, the settings screen 510, 520) of the treatment content on the display 158 (step S10). The terminal device 10 determines whether a vibration instruction (for example, a tap operation of the character string 516) directed at the electrical treatment device 20 has been received via the input device 156 (step S12).

If the vibration instruction has not been received (NO in step S12), then the process of step S16 is executed. If the vibration instruction has been received (YES in step S12), the terminal device 10 instructs the target electrical treatment device 20 associated with the character string 516 to vibrate the case 4a (step S14). Next, the terminal device 10 determines whether a confirmation instruction (for example, a tap operation of the confirmation button 529) of the treatment content has been received via the input device 156 (step S16).

If the confirmation instruction has not been received (NO in step S16), then the terminal device 10 returns to the process of step S10. If the confirmation instruction has been received (YES in step S16), the terminal device 10 displays the confirmation screen (for example, the confirmation screen 610) of the treatment content on the display 158 (step S18). The terminal device 10 determines whether a vibration instruction (for example, a tap operation on any of the objects 612 to 616) directed at the electrical treatment device 20 has been received via the input device 156 (step S20).

If the vibration instruction has not been received (NO in step S20), then the process of step S24 is executed. If the vibration instruction has been received (YES in step S20), the terminal device 10 instructs the target electrical treatment device 20 associated with the selected object to vibrate the case 4a (step S22). Then, the terminal device 10 determines whether a swap instruction (for example, a swap operation for the object 614 and the object 616) of the treatment content has been received via the input device 156 (step S24).

If the swap instruction has not been received (NO in step S24), the terminal device 10 executes the process of step S28. If the swap instruction has been received (YES in step S24), the terminal device 10 swaps the treatment contents (step S26) and determines whether a start treatment instruction (for example, a tap operation on the start button 624) has been received (step S28).

If the start treatment instruction has not been received (NO in step S28), then the terminal device 10 returns to the process of step S18. If the start treatment instruction has been received (YES in step S28), the terminal device 10 instructs the electrical treatment devices 20 to treat the user in accordance with the corresponding treatment content (step S30) and displays the in-treatment screen (for example, the in-treatment screen 710) on the display 158 (step S32). Then, the terminal device 10 determines whether a vibration instruction (for example, a tap operation on any of the objects 612 to 616) directed at the electrical treatment device 20 has been received via the input device 156 (step S34).

If the vibration instruction has not been received (NO in step S34), then the process of step S38 is executed. If the vibration instruction has been received (YES in step S34), the terminal device 10 instructs the target electrical treatment device 20 associated with the selected object to vibrate the case 4a (step S36).

The terminal device 10 determines whether the treatment has ended via the input device 156 (step S38). For example, when the treatment time elapses or a stop treatment instruction is received from the user, the terminal device 10 determines that treatment has ended. If the treatment has not ended (NO in step S38), then the terminal device 10 returns to the process of step S32. If the treatment has ended (YES in step S38), then the terminal device 10 ends the process.

Advantages

According to the present embodiment, even in a case where a plurality of pads are attached to treatment sites of a user, the user can make the electrical treatment devices 20 vibrate via a tap operation on the screen of the terminal device 10. In this way, not only can the user easily set the desired treatment content for each treatment site, but also a setting mistake of the treatment content can be prevented. Moreover, the user does not have to know which electrical treatment device 20 is attached to which treatment site before attaching the pads of the electrical treatment devices 20 to the treatment sites.

According to the present embodiment, the electrical treatment devices 20 can be vibrated via a tap operation on the settings screen of the treatment content, the confirmation screen of the treatment content, and the in-treatment screen. Thus, the user is able to constantly confirm whether the desired treatment content is set for each treatment site.

Other Embodiments

In the embodiments described above, a program may be provided that causes a computer to function and execute controls such as those described in the flowcharts described above. Such a program can also be provided as a program product stored on a non-temporary computer-readable recording medium attached to a computer, such as a flexible disk, a compact disk read only memory (CD), a secondary storage device, a main storage device, and a memory card. Alternatively, a program may be provided, which is stored on a recording medium such as a hard disk built into a computer. The program may also be provided by download via a network.

With the program, required modules from among program modules provided as part of the computer operating system (OS) may be called in a predetermined sequence at a predetermined timing to execute processing. In this case, the modules described above are not included in the program itself, and the process is executed in cooperation with the OS. Programs that do not include such modules may also be included in the program according to the present embodiment.

In addition, the program according to the present embodiment may be provided integrated into a part of a different program. In this case as well, the program according to the present embodiment per se does not include the modules included in the different program described above, and the process is executed in cooperation with the different program. Such a program integrated in a different program shall also be within the scope of the program according to the present embodiment.

The configuration given as an example of the embodiment described above is an example configuration of the present invention. The configuration can be combined with other known technology, and parts thereof may be omitted or modified within the scope of the present invention. Furthermore, the processes and configurations of other embodiments may be employed as appropriate to the embodiments described above.

The embodiments described herein are illustrative in all respects and are not intended as limitations. The scope of the present invention is indicated not by the descriptions above but by the claims and includes all meaning equivalent to the scope and all changes within the scope.

REFERENCE SIGNS LIST

2 Pad
2H Through hole
2X Attachment portion
2Y Treatment portion
2a Conductive layer
3 Holder
4 Main body portion
4a Case
5 Guiding/engagement portion
10 Terminal device
20A, 20B, 20C Electrical treatment device
21 Body-side portion
22 Pad side electrode portion
23 Window portion
30 Network
31 Pad holding portion
32 Wall portion
33 Interlock pin
41 Side surface
43 Main body portion side electrode portion
48S Switch
51 Protrusion
52 Groove portion
102 Input unit
104 Display control unit
106 Vibration instruction unit
108 Treatment content setting unit
110 Treatment instruction unit
152 Processor
154 Memory
156 Input device
158 Display
160 Wireless communication unit
162 Communication antenna
164 Memory interface
165 Storage medium
168 Speaker
170 Microphone
311 Upper surface
312 Positioning protrusion
510, 520 Settings screen
512, 514 Mode selection button
516, 526 Character string
521 Vertical groove portion
522 Lateral groove portion
523, 524, 525 Course selection button
527 Settings button
528, 530, 730, 732 Button
529 Confirmation button
610 Confirmation screen
612, 614, 616, 618, 620, 622, 718, 720, 722 Object
624 Start button
626 Reset button
710 In-treatment screen
740 Stop button
1000 Treatment system

The invention claimed is:

1. A terminal device configured to wirelessly communicate with electrical treatment devices, each one of the electrical treatment devices comprising a case and a vibration source configured to vibrate the case, the terminal device comprising:
a processor configured to:
display, in a single display, image information associated with the each one of the electrical treatment devices on a display of the terminal device;
receive a selection of image information associated with one of the electrical treatment devices and instruct the one of the electrical treatment devices that was selected to vibrate the case of the one of the electrical treatment devices; and
set a treatment content performed by the each one of the electrical treatment devices in accordance with an instruction from the user to set the treatment notified by vibration of the case.

2. The terminal device according to claim 1, wherein the processor is further configured to
instruct the each one of the electrical treatment devices to treat the user in accordance with a treatment content corresponding to the each one of the electrical treatment devices.

3. The terminal device according to claim 2, wherein
the processor is further configured to swap a first treatment content corresponding to a first electrical treatment device of the electrical treatment devices and a second treatment content corresponding to a second electrical treatment device of the electrical treatment devices in accordance with an instruction from the user to swap the first treatment content and the second treatment content; and
when the first treatment content and the second treatment content have been swapped, the processor is further configured to instruct the first electrical treatment device and the second electrical treatment device to treat the user in accordance with the first treatment content and the second treatment content which have been swapped.

4. The terminal device according to claim 2, wherein
when one of the electrical treatment devices is performing treatment in accordance with the treatment content that is set, the processor is further configured to instruct the one of the electrical treatment devices to vibrate the case on the basis of image information associated with the one of the electrical treatment device being selected; and
the treatment content comprises a treatment mode in which an electrical stimulation that does not cause muscle contraction is provided to a treatment site.

5. The terminal device according to claim 1, wherein
when image information associated with a predetermined electrical treatment device of the electrical treatment devices is associated with a predetermined treatment content, the processor is further configured to set the predetermined treatment content as a treatment content performed by the predetermined electrical treatment device.

6. A control method of a terminal device configured to wirelessly communicate with electrical treatment devices, each one of the electrical treatment devices comprising a case and a vibration source configured to vibrate the case, the control method comprising:
displaying, in a single display, image information associated with the each one of the electrical treatment devices;
receiving a selection of image information associated with one of the electrical treatment devices and instructing the one of the electrical treatment devices that was selected to vibrate the case of the one of the electrical treatment devices;
and
setting a treatment content performed by the each one of the electrical treatment devices in accordance with an instruction from the user notified by vibration of the case.

7. A non-transitory recording medium storing a program executed by a computer of a terminal device configured to wirelessly communicate with electrical treatment devices, each one of the electrical treatment devices comprising a case and a vibration source configured to vibrate the case, the program causing the computer to execute:
displaying, in a single display, image information associated with the each one of the electrical treatment devices;
receiving a selection of image information associated with one of the electrical treatment devices and instructing the one of the electrical treatment devices that was selected to vibrate the case of the one of the electrical treatment devices;
and
setting a treatment content performed by the each one of the electrical treatment devices in accordance with an instruction from the user notified by vibration of the case.

8. A treatment system, comprising:
electrical treatment devices; and
a terminal device configured to wirelessly communicate with the electrical treatment devices; wherein
each one of the electrical treatment devices comprises a case and a vibration source configured to vibrate the case, and
the terminal device comprises
a processor configured to:
display, in a single display, image information associated with the each one of the electrical treatment devices on a display of the terminal device;
receive a selection of image information associated with one of the electrical treatment devices and instruct the one of the electrical treatment devices that was selected to vibrate the case of the one of the electrical treatment devices;
and
set a treatment content performed by the each one of the electrical treatment devices in accordance with an instruction from the user notified by vibration of the case,
wherein only the case of the one of the electrical treatment devices that was selected vibrates in response to the instruction.

9. The terminal device according to claim 1,
wherein the image information includes identifying information identifying each one of the electrical treatment devices, and
wherein the processor is further configured to:
receive an indication of a selection of the displayed identifying information of the only one of the electrical treatment devices, and
change the display, in response to the received indication of the selection, to display the treatment content performed by the each one of the electrical treatment devices.

* * * * *